United States Patent
Pillow et al.

(10) Patent No.: US 7,723,553 B2
(45) Date of Patent: May 25, 2010

(54) LIGHT EMITTING DEVICE AND COMPOUNDS FOR USE THEREIN

(75) Inventors: Jonathan N. G. Pillow, Cambridge (GB); Michael Frampton, Oxford (GB)

(73) Assignee: CDT Oxford Limited, Cambridgeshire (GB)

( * ) Notice: Subject to any disclaimer, the term of this patent is extended or adjusted under 35 U.S.C. 154(b) by 742 days.

(21) Appl. No.: 11/520,096

(22) Filed: Sep. 12, 2006

(65) Prior Publication Data

US 2007/0073093 A1 Mar. 29, 2007

Related U.S. Application Data

(63) Continuation of application No. 10/495,443, filed as application No. PCT/GB02/05176 on Nov. 15, 2002, now abandoned.

(30) Foreign Application Priority Data

Nov. 16, 2001 (GB) ................................. 0127461.2
Sep. 7, 2002 (GB) ................................. 0220844.5

(51) Int. Cl.
*C07C 13/32* (2006.01)
(52) U.S. Cl. ............................. 585/27; 585/26; 428/917
(58) Field of Classification Search .................... 585/27, 585/26
See application file for complete search history.

(56) References Cited

U.S. PATENT DOCUMENTS 4,769,292 A 9/1988 Tang et al. .................. 428/690
5,061,569 A 10/1991 VanSlyke et al. ............ 428/457
5,077,142 A 12/1991 Sakon et al. ................ 428/690
5,085,946 A 2/1992 Saito et al. .................. 428/690

(Continued)

FOREIGN PATENT DOCUMENTS

EP 676 461 A2 10/1995

(Continued)

OTHER PUBLICATIONS

Allen et al., "The Structures of Certain Highly Arylated Indenones and Their Behavior with Bromine," *Communication No. 856 from the Kodak Research Laboratories*, vol. 64:2127-2130 (May 29, 1942).

(Continued)

*Primary Examiner*—Ellen M McAvoy
(74) *Attorney, Agent, or Firm*—Marshall, Gerstein & Borun LLP

(57) ABSTRACT

A light emitting device comprising at least one compound of formula (I), (II) or (III) wherein $R_1$ and $R_2$, which may be the same or different, are organic substituents not including H, and wherein $R_3$ and $R_5$ are each independently selected from halo and organic substituents not including H, and wherein $R_4$, $R_6$, $R_7$, $R_8$, $R_9$, and $R_{10}$ are each independently selected from H, halo, and organic substituents, wherein any two or more of $R_1$, $R_2$, $R_3$, $R_4$, $R_5$, $R_6$, $R_7$, $R_8$, $R_9$, and $R_{10}$ may optionally be fused together to form a ring system, provided that one of $R_3$ and $R_5$ is not part of a fused ring system, and provided that $R_1$ and $R_2$ are not fused to each other to form a ring system, and wherein one but not both of either (a) $R_3$ and $R_4$, or (b) $R_5$ and $R_6$, are fused to each other to form a ring system.

8 Claims, 1 Drawing Sheet

U.S. PATENT DOCUMENTS

| | | | |
|---|---|---|---|
| 5,130,603 A | | 7/1992 | Tokailin et al. .............. 313/504 |
| 5,391,790 A | * | 2/1995 | Rohrmann et al. ............ 556/28 |
| 5,840,217 A | | 11/1998 | Lupo et al. .................. 252/583 |
| 6,139,484 A | * | 10/2000 | Biagini et al. ............... 556/453 |
| 6,365,764 B1 | * | 4/2002 | Resconi et al. ................ 556/87 |
| 6,541,584 B1 | * | 4/2003 | Resconi ...................... 526/160 |
| 7,186,870 B2 | * | 3/2007 | Singer et al. .................. 585/27 |
| 7,338,721 B2 | * | 3/2008 | Suzuki et al. ............... 428/690 |

FOREIGN PATENT DOCUMENTS

| | | |
|---|---|---|
| JP | 03-168294 | 7/1991 |
| JP | 04-178488 | 6/1992 |
| JP | 06-228552 | 8/1994 |
| JP | 2001-307880 | 11/2001 |
| WO | WO 97/33323 | 9/1997 |

OTHER PUBLICATIONS

Hosokawa et al., "Highly Efficient Blue Electroluminescence from a Distyrylarylene Emitting Layer with a New Dopant," *Appl. Phys. Lett.* 67 (26):3853-3855 (Dec. 25, 1995).

Koelsch, "Syntheses With Triarylvinylmagnesium Bromides. Pentaarylallyl Alcohols," *Contribution from the Converse Memorial Laboratory of Harvard University*, vol. 54, pp. 3384-3389 (Aug. 5, 1932).

Larock et al., "Synthesis of Indenones via Palladium-Catalyzed Annulation of Internal Alkynes," *J. Org. Chem.*, 58:4579-4583 (1993).

Spreitzer et al., "White and Blue Temperature Stabile and Efficient OLEDs using Amorphous Spiro Transport and Spiro Emitting Compounds," *Proceedings of SPIE*, 4105:25-133 (2001).

International Search Report in PCT/GB02/05176 dated Mar. 30, 2003.

Search Report in GB 0127461.2 dated May 16, 2002.

\* cited by examiner

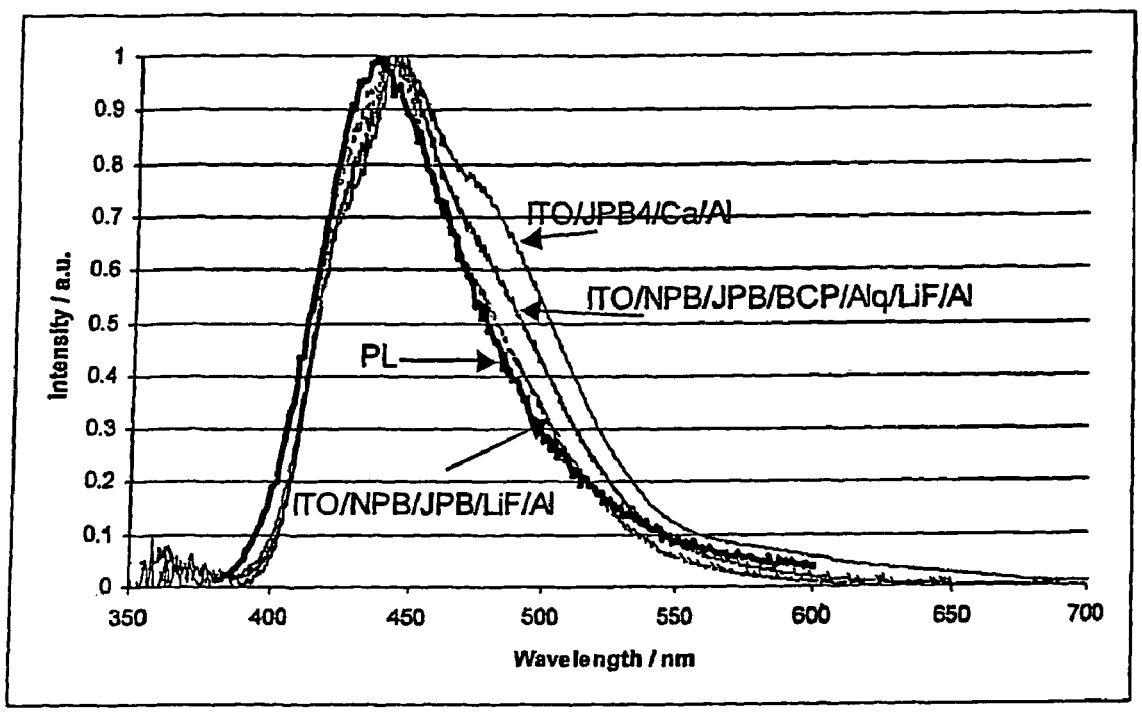

LIGHT EMITTING DEVICE AND COMPOUNDS FOR USE THEREIN

CROSS-REFERENCE TO RELATED APPLICATIONS

This is a continuation of U.S. Ser. No. 10/495,443 filed Oct. 12, 2004 now abandoned, which is the U.S. national phase of International Application No. PCT/GB02/05176 filed Nov. 15, 2002, the entire respective disclosures of which are incorporated herein by reference.

BACKGROUND OF THE INVENTION

1. Field of the Invention

This invention relates to a light emitting device, in particular an organic electroluminescent device, and compounds primarily, although not exclusively, for use therein. These devices may be utilized in flat-panel displays.

2. Description of Related Technology

Organic electroluminescent (EL) displays (or organic light emitting diodes (OLEDs)) have been attracting much attention as a potential alternative to liquid-crystal displays for a number of flat panel display applications. In essence an organic EL device comprises a thin organic layer sandwiched between two electrodes, such that when a current is passed between the electrodes light is emitted from the organic material. The organic material can be macromolecular or a molecular species. In the most efficient devices there are typically a number of organic layers between the electrodes, for example a hole transporting layer, a luminescent layer and an electron transporting layer.

Volatile molecular compounds have the advantage that they can be deposited by thermal evaporation. This allows known techniques (e.g. shadow masking) to be used to form pixellated displays. The luminescent layer may be a homogeneous film, or may consist of a host and a dopant.

Although OLEDs have been under development since the late 1980s there is still scope for improved emissive and charge transporting materials. To make a full color display there is a need for efficient blue, red and green emitters that meet the NIST or PAL color coordinate standards, and that these materials have a long operating lifetime. The lifetime of current blue emitters is less than is required for many applications.

It is known that recrystallization of the organic films is one failure mechanism and hence that a high glass transition temperature (Tg) is a necessary requirement for a long device lifetime.

Among the best-known blue emitting compounds for organic EL devices are stilbene and triarylethylene derivatives such as 4,4'-bis(2,2'-diphenylvinyl) biphenyl (DPVBi) (Idemitsu Kosan U.S. Pat. No. 5,130,603 and App. Phys. Lett. 1995, 67(26), 3853-3855). DPVBi devices can be made more efficient by doping the DPVBi layer with a blue dye, but this adds complexity to the device fabrication. The resulting color will depend on the blue dye used. The spiro compound spiro-DPVBi has an improved Tg relative to DPVBi; however the color is still not as blue as is desired for a full-color display. The emission maximum is at 470 nm and the FWHM (Full Half Width Maximum) is greater than 80 nm (Proceedings of SPIE Vol 4105 (2001) p125-133).

It would be advantageous to enhance the color purity, efficiency and lifetime, particularly of blue emitting EL devices.

The non-planar structure of the compounds of this invention makes the compounds surprisingly volatile for their size which allows larger molecules to be used which have a greater chance of having a high Tg. This allows stable amorphous films to be formed by thermal evaporation. Some of the compounds are optically active, which can have the benefit that a mixture of enantiomers will tend to form a glassy film rather than a polycrystalline film. Alternatively a non-optically active compound may be easier to purify.

EL devices have been made with novel molecules that emit deep blue light.

The indenes included in the invention were designed to offer superior advantages over compounds that contain the more standard stilbene group. Many stilbene-containing compounds have been shown to have excellent emission characteristics in electroluminescent devices. There are however two significant disadvantages with the stilbene system. Firstly, although some twisting does occur around the axial bonds, the molecules are comparatively planar. This means that neighboring molecules can be packed closely together—a process that is well known to allow the introduction of intermolecular electronic orbitals, the broadening of electronic spectra, and the reduction of luminescent efficiency. Close approach of molecules can also enhance intermolecular electrochemical reactions, which are likely to be a significant cause of electroluminescent lifetime loss.

The second problem with stilbene systems is associated with the slightly twisted nature of the stilbene. Twisting oscillations (libration) along the axis means that there is a bigger distribution of molecular orbitals, which leads to a broadening of the electronic spectra of the material.

The compounds of the invention were therefore designed to address both these problems, with the aim of preparing a family of molecules that have narrower electronic spectra—particularly in the electroluminescence spectra—and that have better electrochemical stability that could provide longer EL lifetimes.

Indenes differ from the stilbenes by including the disubstituted bridging carbon atom. This achieves two purposes. Firstly, because half of the former stilbene is now enclosed in a 5-membered ring, the indene molecule is significantly more rigid which means that there are far fewer degrees of freedom for the molecule, leading to narrower electronic spectra. Secondly, because the two substituting groups overhang the faces of the indenes, the main molecular orbitals of the indene are protected from the approach of other molecules, so that intermolecular effects should be greatly reduced.

The idea of using bulky groups in inhibiting molecular packing has been known for a long time. A more relevant case is that of fluorene, where there are also overhanging groups that can protect the molecular faces from packing. However, the use of fluorene in place of biphenyl is a very specific process that cannot be used to enhance the performance of stilbene containing molecules, which are an extremely important separate class of materials for use in OLEDs.

By allowing the development of enhanced versions of stilbene derivatives, this invention opens up significant and novel possibilities for designing compounds for electroluminescent applications.

U.S. Pat. No. 5,840,217 discloses the use of spiro compounds as electroluminescence materials. The compounds are said to have a good solubility in customary organic solvents, improved film-forming properties and a significantly reduced tendency to crystallize. This leads to an increased service life of electroluminescence devices including such compounds.

U.S. Pat. No. 5,077,142 discloses electroluminescent devices comprising a wide variety of compounds which include an aromatic benzene ring, including unsubstituted indenes.

JP 3-168294 describes a compound in which fused cyclic systems are bound to a 5-membered ring having a tetrahedral carbon atom.

Spiro compounds for use in OLEDs are also disclosed in Spreitzel et al, Organic Light-Emitting Materials and Devices Vol 4105 (2001) pp 125-133.

U.S. Pat. No. 5,085,946 discloses the use of various cyclopentadiene derivatives in OLEDs. The substituents are not linked to form a ring system and the operating voltages of the devices disclosed are undesirably high.

JP 2001-307880 discloses spiro compounds for use in OLEDs. Such compounds can be quite difficult to synthesise and limit the substituents that can be used at the tetrahedral carbon position.

SUMMARY OF THE INVENTION

Thus, according to the invention, there is provided a light emitting device comprising at least one compound of formula (I), (II) or (III):

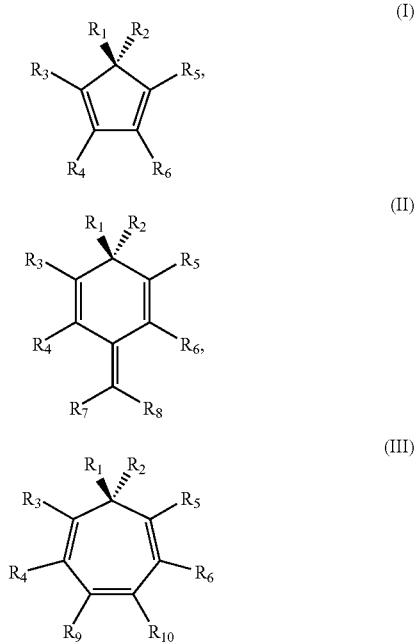

wherein $R_1$ and $R_2$, which may be the same or different, are organic substituents not including H, and wherein $R_3$ and $R_5$ are each independently selected from halo and organic substituents not including H, and wherein $R_4$, $R_6$, $R_7$, $R_8$, $R_9$ and $R_{10}$ are each independently selected from H, halo, and organic substituents, wherein any two or more of $R_1$, $R_2$, $R_3$, $R_4$, $R_5$, $R_6$, $R_7$, $R_8$, $R_9$ and $R_{10}$ may optionally be fused together to form a ring system, provided that one of $R_3$ and $R_5$ is not part of a fused ring system, and provided that $R_1$ and $R_2$ are not fused to each other to form a ring system, and wherein one but not both of either (a) $R_3$ and $R_4$, or (b) $R_5$ and $R_6$, are fused to each other to form a ring system.

Thus, while $R_1$, $R_2$, $R_3$, $R_4$, $R_5$, $R_6$, $R_7$, $R_8$, $R_9$ and $R_{10}$ may be selected as indicated above, when two or more are fused to form a ring system, such a ring system is organic.

BRIEF DESCRIPTION OF THE DRAWING

The sole FIGURE shows EL emission spectra of several exemplary devices of the invention and the photoluminescence spectrum of JPB4a (solid powder).

DETAILED DESCRIPTION

The presence of $R_1$ and $R_2$ on the tetrahedral carbon atom hinders both faces of the conjugated region, helping to prevent pi-stacking and thereby improving the color purity of the emission. Furthermore, by excluding spiro compounds, the synthesis of the compounds is simplified and a greater variety of substituents at the tetrahedral carbon position can be obtained which may allow optimisation of the properties. For example, $R_1$ and $R_2$ could be charge-transporting groups.

There is only one tetrahedral carbon position in each of the 5, 6 or 7-membered rings, and the double bonds are in conjugation.

By way of examples, in formula (II) $R_4$ and $R_7$, or $R_3$ and $R_4$ and $R_7$, or $R_6$ and $R_8$, may be fused to each other to form a ring system, and in formula (III) $R_9$ and $R_{10}$ may be fused to each other to form a ring system.

Preferably, the light emitting device comprises a compound of formula (I).

Preferably $R_3$, $R_4$, $R_5$ and $R_6$ are organic substituents. $R_7$, $R_8$, $R_9$ and $R_{10}$ are preferably independently H or organic substituents.

The organic substituents may be any appropriate group, examples being alkyl, aryl and heteroaryl, each of which may be substituted or unsubstituted. For example, when the substituents are aryl or heteroaryl, they may be substituted by any appropriate group, examples being aryl, heteroaryl, diarylamine, alkyl, cycloalkyl, a fused ring system, halo or haloalkyl groups. Throughout this invention the substituents may themselves optionally be substituted. Similar rings may be formed when any of $R_1$, $R_2$, $R_3$, $R_4$, $R_5$, $R_6$, $R_7$, $R_8$, $R_9$ and $R_{10}$ are fused together to form a ring system, which system is preferably a fused aromatic ring, which may contain a heteroatom.

The alkyl substituent is preferably a $C_{1-6}$ alkyl and may be straight or branched chain, examples being methyl, ethyl, t-butyl or the like.

The aryl groups may, for example, be $C_{6-15}$ aryl groups such as phenyl, 1-naphthyl, 2-naphthyl, fluorene or the like.

The other of $R_3$ and $R_4$, or $R_5$ and $R_6$, which do not form the fused ring system, may in one embodiment be (substituted or unsubstituted) aryl, for example phenyl.

The fused ring system may comprise a fused aromatic ring, for example a benzene ring. Thus, in a preferred embodiment, the light emitting device comprises at least one of the following compounds:

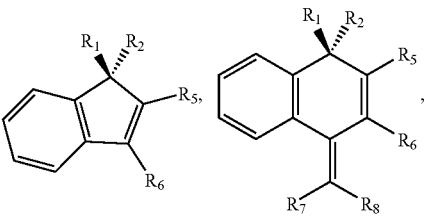

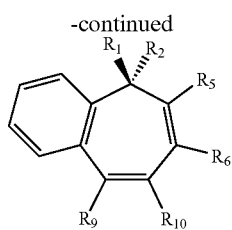

Preferably, the light emitting device comprises a compound of formula (IV):

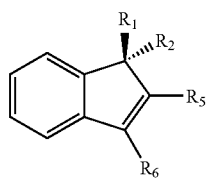

(IV)

$R_1$, $R_2$, $R_5$ and $R_6$ are defined as above. It may have the preferred features mentioned above. In one embodiment $R_1$, $R_2$, $R_5$ and $R_6$ are independently selected from substituted or unsubstituted aryl, benzyl or alkyl and when they are alkyl, they are preferably $C_{1-6}$ alkyl. $R_1$ and $R_2$ are preferably each (substituted or unsubstituted) aryl. $R_5$ and $R_6$ are preferably each (substituted or unsubstituted) aryl, for example phenyl.

It is preferred that the compound evaporates or sublimes in the temperature range of 200-400° C. at a reduced pressure, for example $10^{-6}$ mbar.

Preferably, the glass transition temperature of the compound is greater than 80° C. and the melting point is preferably greater than 100° C., for example greater than 130° C.

The light emitting device is generally an organic electroluminescent device and further comprises an anode and a cathode, wherein the compound is sandwiched therebetween.

According to a further aspect of the invention, there is provided the use of a compound of formula (I), (II) or (III) as a luminescent material in a light emitting device.

According to a further aspect of the invention, there is provided the use of a compound of formula (I), (II) or (III) as an electron transport material in a light emitting device.

According to a further aspect of the invention, there is provided the use of a compound of formula (I), (II) or (III) as a hole transport material in a light emitting device.

According to a further aspect of the invention there is provided a compound of formula (V):

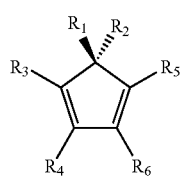

(V)

wherein $R_3$ and $R_4$ are fused to each other to form a substituted or unsubstituted fused aromatic ring, and wherein $R_1$, $R_2$, $R_5$ and $R_6$, which may be the same or different, are independently selected from aryl or heteroaryl, each of which is optionally substituted by aryl, heteroaryl, diarylamine, alkyl, cycloalkyl, a fused ring system, halo, haloalkyl, cyano and alkyloxy groups, provided that $R_1$ and $R_2$ are not fused to each other to form a ring system, and provided that $R_5$ and $R_6$ are not fused to each other to form a ring system, and provided that $R_1$, $R_2$, $R_5$ and $R_6$ are not all phenyl.

Such compounds are particularly useful when used in a light emitting device, although other uses are not excluded.

Each substituent may itself be substituted as necessary.

In a preferred embodiment, the aryls are $C_{6-15}$ aryls, specific examples being phenyl, 1-naphthyl, 2-naphthyl, and fluorene. The heteroaryls are preferably selected from oxadiazole, carbazole, triazole, oxazole, thiazole or benzothiazole and, in general, aryl groups are more preferred than heteroaryl groups.

The alkyl substituent is preferably a $C_{1-6}$ straight or branch chain alkyl group, specific examples being methyl, ethyl, and t-butyl.

In a preferred embodiment, the fused ring system substituent is a hydrocarbon ring system. Preferably, at least one ring of the fused ring system substituent is not aromatic, examples being indene, perinaphthene, tetrahydronaphthalene.

Diarylamine substituents are preferably selected from diphenylamine, ditolylamine, dinaphthylamine, phenyltolylamine, phenylnaphthylamine, or the like.

In a preferred embodiment, $R_3$ and $R_4$ are fused to each other to form a 6-membered aromatic (benzene) ring. The ring may be substituted by any suitable substituent, even including one or more further rings fused to it.

The following compound has been found to be particularly useful in the invention:

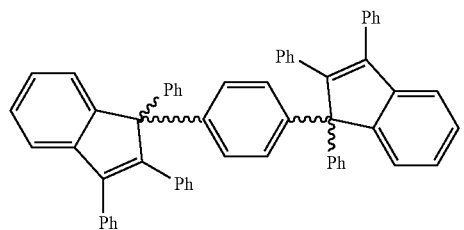

This compound has two chiral centers and can therefore exist in (S,S), (R,R) and (S,R) stereoisomers. It has been found that two reaction products can be isolated, having crystalline and glassy forms, and it is believed that these correspond to the (S,R) and mixed (S,S) and (R,R) isomers respectively. Both molecules show bright blue fluorescence. The crystalline form has a melting point of 349° C. and a Tg of 149° C.

An alternative compound which has been found to be useful in the invention is:

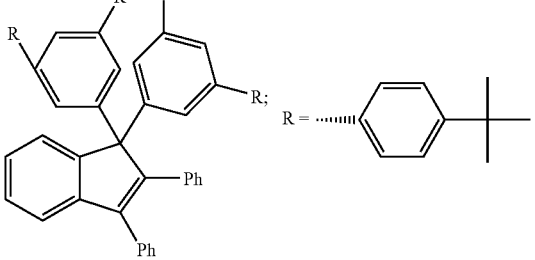

The $R_1$ and $R_2$ substituents at the tetrahedral carbon position are 3,5-bis(4-tert-butylphenyl)phenyl groups which are a type of first generation dendron. The attachment of dendrons at these positions provides a way of making the compound soluble and suitable for solution processing, and features of the dendrons can be modified to control the processing properties without significantly altering the emission characteristics. This particular compound can be spin-coated to form a good quality film, and has a blue PL (photoluminescence) emission spectrum.

A variety of methods can be used to prepare compounds of the invention, and the following are examples.

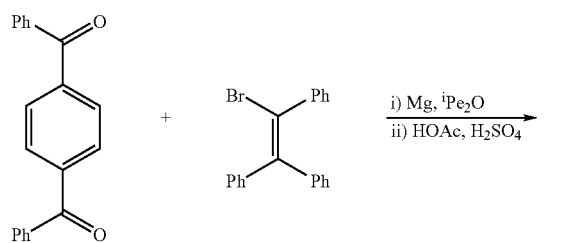

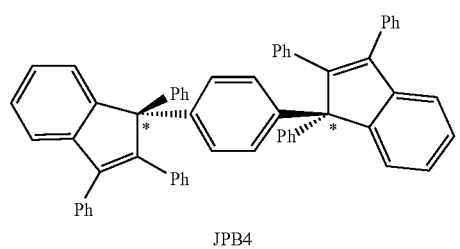

JPB4 ii) Grignard attack onto indanones

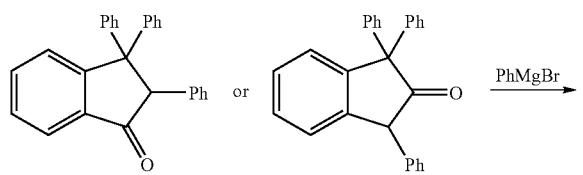

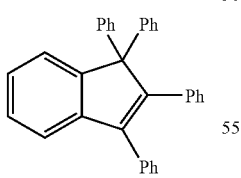

iii) Cyclisation of pentaarylpropanones (A):

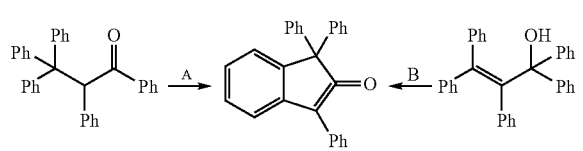

iv) Closure of pentaarylallyl alcohols (B):

Preparation of the starting allyl alcohol has been demonstrated from the bromoethylene:

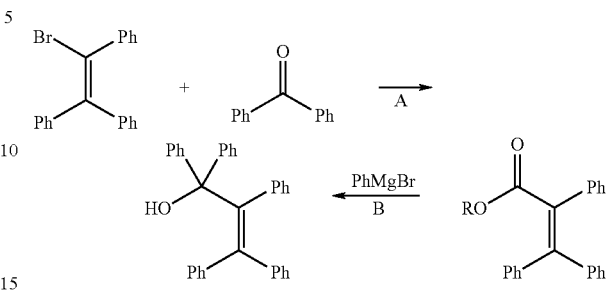

v) Pd catalyzed addition to o-bromoaldehydes.

A reaction between 2-bromobenzaldehyde and diphenylacetylene has reportedly given 2,3-diphenylindenone in good yield (Larock et al, J. Org. Chem. 1993, 58, 4579-4583). This simple reaction should work easily with other systems, including the more complicated 2,5-dibromoterephthaldehyde.

vi) Friedel-Krafts cyclization with acyl chlorides.

A similar, but simpler reaction involves the Friedel-Krafts reaction of an acyl chloride with diphenylacetylene.

In general, an organic electroluminescent device comprises an anode and a cathode separated from each other by an organic layer that comprises at least one luminescent material that emits light when a voltage is applied across the electrodes. The organic layer comprises, in its simplest common form, a hole injecting and transporting zone adjacent to the anode and an electron injecting and transporting zone adjacent to the cathode. More usually, however, the organic layer will comprise several layers or zones, each performing as is well known in the art a different function from its neighboring zone. As is also well known in the art, the luminescent zone may comprise a homogeneous material or a host material containing a luminescent dopant. In these respects, reference is made to U.S. Pat. No. 4,769,292 and U.S. Pat. No. 5,061,569. The compounds of the invention have utility in such electroluminescent devices in the luminescent zone, in a hole injecting and transporting zone or in an electron injecting and transporting zone.

Several general problems have been encountered in many OLED materials, which this invention may go some way towards addressing:

Thermal stability: It is important that the molecule can be stable as an amorphous film at temperatures up to 130° C., while still being sufficiently volatile for simple evaporation. The molecules described in this invention are known to be extremely thermally stable. Due to the non-planar nature of the molecules, even large types of this molecule are surprisingly volatile, which allows larger molecules to be used which have a greater chance of having a high Tg. Alternatively, the ease with which optical activity can be introduced means that fully amorphous glasses can be synthesised that have no tendency to crystallise at all.

Color purity: Many planar organic molecules can form π-stacking aggregates, either with each other or with materials in neighboring films. The result is the introduction of lower energy excitation states that can broaden the emission spectrum (sometimes considerably) and give reduced light intensity. The tetrahedral carbon atom in the compounds of the present invention limits the approach of other molecules, reducing this π-stacking and allowing much purer colors to be emitted. Molecules show excellent blue emission in PL. Optimization to give other colors is believed to be comparatively simple.

Brightness: Compared with a triarylethylene or with a stilbene, in some instances indenes have been shown to have much higher PL efficiencies. This has been explained by their much more rigid structure, which reduces rotations that can lead to non-radioactive decay.

Color tuning: By having what is effectively a triarylethylene compound, a significant amount of conjugation area can be confined to a relatively small volume, so that the same emission color can be achieved from a smaller molecule than would be possible with existing systems. The possibilities for extending the conjugation length to obtain colors such as green, orange and yellow, while still having a volatile molecule, are therefore increased. More subtle effects on the emission color can be achieved by minor adjustments to the bond angles and to the exact nature of the substituents, thereby allowing accurate tuning of the band-gap and the color of the emission.

EXAMPLE 1

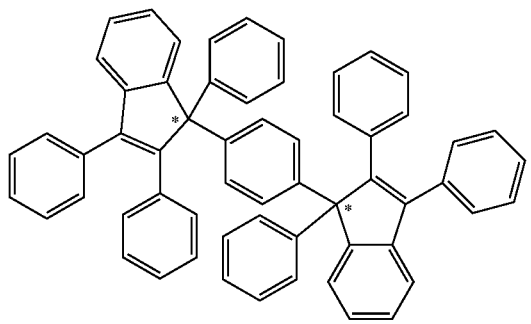

[JPB4a=(R,S) isomer; JPB4b=mixed (S,S) and (R,R) isomers]

Preparation of (R,S)-1,4-bis(1,2,3-triphenyl-1H-inden-1-yl)benzene, (code JPB4a)

A mixture of bromotriphenylethylene (73.00 g, 218 mmoles), magnesium turnings (5.292 g, 218 mmoles) and anhydrous isoamyl ether (~200 cm$^3$) was heated slowly over 90 minutes until almost at reflux, by which time almost all of the magnesium had disappeared. 1,4-dibenzoylbenzene (21.00 g, 73.3 mmoles) was then added and the reaction mixture was heated in an oil bath at 165° C. for 2 hours. After cooling, aqueous ammonium chloride (1 M, 350 cm$^3$) and dichloromethane (350 cm$^3$) were added. The aqueous layer was separated and extracted with dichloromethane (5×100 cm$^3$) and the combined organic layers were washed with aqueous ammonium chloride (2×100 cm$^3$) and water (3×100 cm$^3$) and evaporated to give an orange oil. This oil was triturated with diethyl ether (300 cm$^3$), left to stand overnight, filtered, rinsed with diethyl ether and dried under suction to give a pale pink powder. The crude product (15.36 g) was then recrystallized from dichloromethane/hexane to give a white powder (10.01 g) of 1,4-bis(1-hydroxy-1,2,3,3 tetraphenyl-prop-2-en-1-yl)benzene. This powder was mixed with acetic acid (250 cm$^3$) and heated to reflux. Sulphuric acid (concentrated, 5 cm$^3$) was then added and the reaction mixture was heated at reflux for a further 80 minutes and then allowed to cool. The white precipitate was filtered from the supernatant liquid which was used subsequently for the preparation of the mixed (S,S) and (R,R) isomers. Meanwhile, the isolated white precipitate was rinsed with acetic acid/water (1:1), water, ethanol and diethyl ether before being dried under suction to give a white powder (6.02 g), of which the infra-red spectrum did not show the presence of any peaks at ~3600 cm$^{-1}$ that could correspond to the continued presence of the hydroxyl moiety. The white solid was recrystallized from dichloromethane/hexane to give white crystals (2.43 g) and these were sublimed twice in succession at 5×10$^{-8}$ mbar and 300° C. to give white crystals (1.40 g, 3%, m.p. 346-347° C.) that co-chromatographed with and had an identical i.r. spectrum to an authentic sample of (R,S)-1,4-bis(1,2,3-triphenyl-IH-inden-1-yl)benzene, m.p. 346-49° C. (Found: C, 93.9; H, 5.5. C$_{60}$H$_{42}$ requires C, 94.5; H, 5.6%; δH(500 MHz; CDCl$_3$) 6.7-7.3 (42H, m, molecule); νmax (DATR)/cm$^{-1}$ 694s, 1028w, 1443m, 1489m, 1598w, 3057w; m/z (FAB) 762.4 (M+, 25%); DSC (T$_g$=149° C., T$_m$=353° C.); TGA (stable in air >350° C.); Solid PL (CIE x=0.16, y=0.10).

EXAMPLE 2

Preparation of (R,R;S,S)-1,4-bis(1,2,3-triphenyl-1H-inden-1-yl)benzene, (Code JPB4b)

The acetic acid mother liquor from the procedure described above was diluted with water and the precipitate thereby released was filtered, combined with the mother liquors from the recrystallizations in the previous procedure and dried under vacuum. Purification was by a combination of repeated recrystallizations and evaporations in a manner similar to that for the (R,S) isomer-described above, which gave a pale yellow glass (2.173 g, 4%) of a racemic mixture of (S,S)-1,4-bis (1,2,3-triphenyl-1H-inden-1-yl)benzene and (R,R)-1,4-bis (1,2,3-triphenyl-1H-inden-1-yl)benzene, m.p. 130-150° C. (Found: C, 94.5; H, 5.5 C$_{60}$H$_{42}$ requires C, 94.5; H, 5.6%); δH(500 MHz; CDCl$_3$) 6.6-7.5 (42H, m, molecule); νmax (DATR)/cm$^{-1}$ 695s, 1029w, 1422m, 1490m, 1597w, 3056w; DSC (T$_m$=130-140° C.); TGA (stable in air >350° C.); Solid PL (CIE x=0.15, y=0.10).

EXAMPLE 3

Experimental

Device Fabrication and Testing

Indium tin oxide (ITO) coated glass substrates, which can be purchased from several suppliers, for example Applied Films, USA or Merck Display Technology, Taiwan, were cleaned and patterned using a standard detergent and standard photolithography processes. The substrates used in the following examples measured 4"×4" and 0.7 mm thick, the ITO was 120 nm thick, and the ITO was patterned to produce 4 devices on each substrate each with an active light emitting area of 7.4 cm$^2$. After the final stage of the photolithography process, i.e., the removal of the photoresist, the substrates were cleaned in a detergent (3 vol. % Decon 90), thoroughly rinsed in deionized water, dried and baked at 105° C. until required. Immediately prior to the formation of the device the treated substrate was oxidized in an oxygen plasma etcher. By way of example an Emitech K1050X plasma etcher operated at 100 Watts for two minutes is adequate. The substrate and shadow mask was then immediately transferred to a vacuum deposition system where the pressure is reduced to below $10^{-6}$ mbar. The organic layers were evaporated at rates between 0.5-1.5 Å/s. Then the mask was changed to form a cathode with a connection pad and no direct shorting routes. The cathode was deposited by evaporating 1.5 nm of LiF at a rate of 0.2 Å/s followed by 150 nm of aluminium evaporated at a rate of 2 Å/s.

Some devices were encapsulated at this stage using an epoxy gasket around the edge of the emissive area and a metal lid. This procedure was carried out in dry nitrogen atmosphere. The epoxy was a UV curing epoxy from Nagase, Japan.

Current/voltage, Brightness/Voltage measurements were performed using a Keithley 2400 Source measure unit and a calibrated photodiode through a Keithley multimeter programmed from an IBM compatible PC. The EL emission spectrum was measured using an Oriel ccd camera.

Results

Seven devices using JPB4 have been made:

| Device | Color | CIE coords | Cd/A | Lm/W |
|---|---|---|---|---|
| 1 ITO/JPB4a/Al | Blue | | | |
| 2 ITO/JPB4a/Ca/Al | Blue-purple | 0.19, 0.17 | | |
| 3 ITO/NPB/JPB4a/LiF/Al | Blue | 0.16, 0.11 | 0.2 | 0.08 |
| 4 ITO/NPB/JPB4a/Alq/LiF/Al | Blue → green with current | | 2.8 | 1.4 |
| 5 ITO/NPB/JPB4a/BCP/Alq/LiF/Al | Blue | 0.16, 012 | 1.6 | 0.6 |
| 6 ITO/JPB4a/Alq/LiF/Al | Alq green | 0.32, 0.56 | 3.4 | 1.9 |
| 7 ITO/JPB4b/Alq/LiF/Al | Alq green | | 3.5-4.6 | 1.3-1.9 |

ITO = indium tin oxide
NPB = N,N'-di(1-naphthyl)-N,N'-diphenyl-{1,1'-biphenyl}-4,4'-diamine
Alq = tris(8-quinolinato)aluminium The sole FIGURE shows EL emission spectra of devices 2, 3, and 5 and the photoluminescence emission spectrum of JPB4a (solid powder). All devices are un-optimized. The following features are to be noted.

Comparatively efficient blue emission is exhibited 0.6 lm/W (or 1.6 cd/A). The EL blue emission of JPB4a (devices 3 and 5) is almost identical to PL emission (both solid state).

Excellent PAL blue color is shown, which is similar to PL where the CIE coordinates are (0.16, 0.10).

A narrow emission spectrum (about 75 nm) half-width is shown.

Almost no broadening suggests that the 3D structure of JPB4a limits π-stacking and hence excimers. In addition, if excimers are removed, then intermolecular reactions should also be removed, therefore leading to an improved lifetime of the device.

When JPB4a or JPB4b is used as a hole transporting layer with Alq as the emissive layer (device 6 and 7 respectively), efficient Alq emission is observed and the device is almost equivalent to those using NPB as a hole transporting layer.

EXAMPLE 4

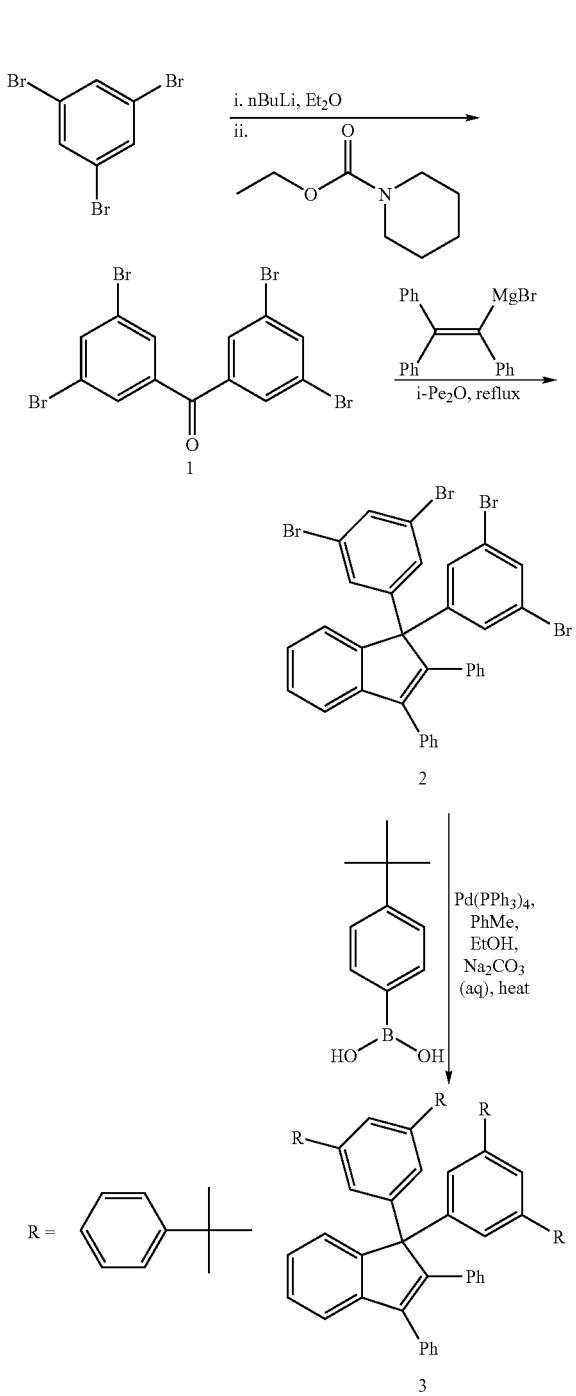

Preparation of 3,5,3',5'-Tetrabromobenzophenone (1)

A solution of 1,3,5-tribromobenzene (50.0 g, 160 mmol) in dry ether (1000 cm$^3$) was cooled to −90° C. under nitrogen in a toluene/liquid nitrogen bath. n-Butyllithium (1.6 M in hexanes, 100 cm$^3$, 160 mmol) was added dropwise before stirring in the cold bath for 1 h. Ethyl piperidine-1-carboxylate (10.061 g, 64.0 mmol) was added dropwise over 20 min and the mixture stirred in the cold bath for a further 20 min, before the mixture was allowed to warm to room temperature and then heated briefly to reflux. Aqueous hydrochloric acid (20%, 500 cm³) was added slowly and the reaction was stirred vigorously and allowed to stand overnight. The aqueous layer was separated and extracted with dichloromethane. The organic layers were combined and the solvent removed. The residue was passed through a plug of silica with dichloromethane. The solvent was removed and the solid was washed with ether and dried under suction. The crude product was then sublimed under vacuum (220° C., 4×10⁻⁷ mbar), then recrystallized from dichloromethane/hexane to give 1 (18.40 g, 58%) as a crystalline powder, mp 208-209° C.

Preparation of 2,3-Diphenyl-1,1-bis(3,5-dibromophenyl)-1H-indene (2)

A mixture of bromotriphenylethylene (14.143 g, 42.19 mmol), magnesium (903 mg, 37.2 mmol) and i-pentylether (100 cm³) was heated to reflux for 1.75 h. Heating was temporarily removed and 1 (14.00 g, 28.12 mmol) was added. The mixture was heated to reflux under nitrogen for 20 h and then allowed to cool. Hexane (100 cm³) was added and the mixture was allowed to stand for 30 min. The resultant precipitate was collected and washed with hexane. The solid was mixed with dichloromethane (200 cm³) and aqueous ammonium chloride (1 M, 200 cm³) and stirred until fully dissolved. The aqueous layer was separated and extracted with dichloromethane (3×30 cm³) and the combined organic layers washed with aqueous ammonium chloride (1 M, 100 cm³) and water (100 cm³), dried over anhydrous magnesium sulphate, filtered and the solvent removed. The residue was triturated with boiling ethanol, cooled and filtered to give 2 (16.34 g, 79%) as a white solid.

Preparation of 2,3-Diphenyl-1,1-bis[3,5-bis(4-tert-butylphenyl)phenyl]-1H-indene (3)

A mixture of 4-tert-butylphenylboronic acid (5.00 g, 28.08 mmol), 2 (3.45 g, 4.68 mmol), tetrakis(triphenylphosphine)palladium(0) (1.08 g, 0.937 mmol), toluene (44 cm³), ethanol (15 cm³) and aqueous sodium carbonate (2 M, 15 cm³) was degassed then heated to 100° C. under nitrogen for 69 h and allowed to cool. The organic layer was separated and washed with aqueous hydrochloric acid (3 M, 20 cm³), water (20 cm³) and brine (20 cm³) and the solvent removed. The residue was dissolved in dichloromethane (150 cm³) and the yellow insoluble material discarded. The filtrate was concentrated and recrystallised form a dichloromethane/ethanol mixture. The resultant solid was purified by column chromatography over silica with dichloromethane/hexanes (1:2) as eluent, and recrystallised from a dichloromethane/ethanol mixture to give 3 (3.69 g, 83%) as a white crystalline solid. ¹H NMR (CDCl₃, 400 MHz, ppm): 1.28 (36H, s, t-butyl), 7.02-7.39 (30H, m, aromatic H), 7.53 (4H, d, J 1.5, branch phenyl 2,6-H) and 7.63 (2H, dd, J 1.5, branch phenyl 4-H).

Compound 3 is photoluminescent and the CIE coordinates of the emission are (0.154, 0.104) for solution (THF), and (0.16, 0.17) for film (spun from chloroform).

The invention claimed is:

1. A compound of formula (V):

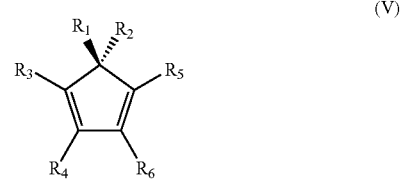

wherein $R_3$ and $R_4$ are fused to each other to form a substituted or unsubstituted fused aromatic ring, and wherein $R_1$, $R_2$, $R_5$ and $R_6$, which may be the same or different, are independently selected from aryl and heteroaryl, each of which is optionally substituted by aryl, heteroaryl, diarylamine, alkyl, cycloalkyl, a fused ring system, halo, haloalkyl, cyano and alkyloxy groups, provided that $R_1$ and $R_2$ are not fused to each other to form a ring system, and provided that $R_5$ and $R_6$ are not fused to each other to form a ring system, and provided that $R_1$, $R_2$, $R_5$ and $R_6$ are not all phenyl.

2. A compound according to claim 1, wherein the aryls are $C_{6-15}$ aryls.

3. A compound according to claim 1, wherein the heteroaryls are selected from oxadiazole, carbazole, triazole, oxazole, thiazole and benzothiazole.

4. A compound according to claim 1, wherein the alkyl substituent is a $C_{1-6}$ straight or branch chain alkyl group.

5. A compound according to claim 1, wherein the fused ring system substituent is a hydrocarbon ring system.

6. A compound according to claim 1, wherein at least one ring of the fused ring system substituent is not aromatic.

7. A compound according to claim 1, wherein $R_3$ and $R_4$ are fused to each other to form a 6-membered aromatic ring.

8. A compound according to claim 1, having the following formula:

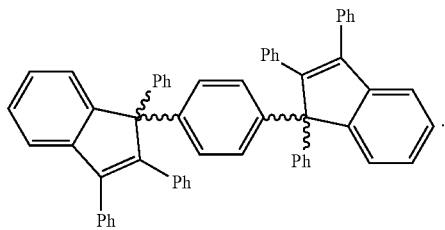

* * * * *

UNITED STATES PATENT AND TRADEMARK OFFICE
CERTIFICATE OF CORRECTION

PATENT NO. : 7,723,553 B2
APPLICATION NO. : 11/520096
DATED : May 25, 2010
INVENTOR(S) : Jonathan N. G. Pillow et al.

Page 1 of 1

It is certified that error appears in the above-identified patent and that said Letters Patent is hereby corrected as shown below:

In the Specification:

At Column 13, line 44, "recrystallised form" should be -- recrystallized from --.

Signed and Sealed this
Twenty-second Day of February, 2011

David J. Kappos
*Director of the United States Patent and Trademark Office*